United States Patent [19]
Smith

[11] 3,971,365
[45] July 27, 1976

[54] BIOELECTRICAL IMPEDANCE MEASURING SYSTEM

[75] Inventor: Leland B. Smith, Arlington Heights, Ill.

[73] Assignee: Beckman Instruments, Inc., Fullerton, Calif.

[22] Filed: Feb. 12, 1973

[21] Appl. No.: 331,770

[52] U.S. Cl. ............................................. 128/2.1 Z
[51] Int. Cl.² ......................................... A61B 5/05
[58] Field of Search .................. 128/2.05 F, 2.05 R, 128/2.05 N, 2.1 R, 2.1 Z, 2.06 B, 2.06 F, 2.06 R

[56] References Cited
UNITED STATES PATENTS

| | | | |
|---|---|---|---|
| 3,316,896 | 5/1967 | Thomasset | 128/2.1 Z |
| 3,340,867 | 9/1967 | Kubicek et al. | 128/2.1 Z |
| 3,498,288 | 3/1970 | Mat et al. | 128/2.1 R |
| 3,556,083 | 1/1971 | Grichnik et al. | 128/2.1 Z |
| 3,599,628 | 8/1971 | Abbenante et al. | 128/2.06 F |
| 3,608,543 | 9/1971 | Longini et al. | 128/2.1 Z |
| 3,742,936 | 7/1973 | Blanie et al. | 128/2.1 Z |

Primary Examiner—William E. Kamm
Attorney, Agent, or Firm—R. J. Steinmeyer; P. R. Harder

[57] ABSTRACT

A bioelectrical impedance measuring system that measures and indicates the impedance of a biological subject, such as one or more human extremities. The system measures and indicates a basal impedance value of the measured subject, and also indicates short temporal variations in the basal value. In the system an excitation signal, derived from an electrical signal source, is coupled to the subject by excitation electrodes and a resulting subject output signal is sensed by receiver electrodes. The subject output signal is electronically subtracted from a reference signal derived from the signal source, and the resulting signal is used to drive a display unit. The system includes a null detector connected to the display unit input, and an automatic gain control unit responsive thereto, connected in the subject output signal path to automatically maintain the system in a nulled condition. With the output of the system adjusted to a null condition the value indicated is proportional to the basal impedance of the subject. The automatic gain control unit includes a lock function generator to hold the variable gain at an instantaneous null establishing a basal value for a desired measurement episode. Consequently, any variations in the nulled signal are indicative of variations in the impedance of the subject. A range indicator is associated with the gain control unit to verify that the subject output signal is within the dynamic range of the gain control unit.

8 Claims, 3 Drawing Figures

BIOELECTRICAL IMPEDANCE MEASURING SYSTEM

BACKGROUND OF THE INVENTION

The present invention relates to a bioelectrical impedance measuring system that measures and indicates the impedance of biological subjects, such as human extremities. More particularly the invention relates to a bioelectrical impedance measuring system that indicates a basal impedance value of the measured subject and also indicates variations in the basal value.

Bioelectrical impedance measurements are well known in the prior art. More particularly, such measurements are conducted for well established clinical purposes such as the measurement of fluid volume changes, estimation of cardiac output, and detection of deep venous thrombosis and peripheral vascular disease. The bioelectrical impedance of a segment of tissue or an extremity of the human body is a measure of the opposition to the flow of an electrical current. When blood pulses into a segment of the body, the electrical impedance of that body segment is changed by the varying amount of blood present. The presence of a slightly increased amount of blood will reduce the impedance of the tissue segment; and, conversely, when blood flows out of the tissure segment, the impedance increases. The bioelectrical impedance may be measured in a variety of ways, such as by applying a minute radio-frequency current to the tissue being monitored and by sensing the alterations that occur in the signal detected from the tissue through use of an instrumentation system. Typical systems are described in U.S. Pat. Nos. 2,111,135; 2,184,511 and 3,149,677 to Bagno, and 3,340,867 to Kubicek et al.

A report titled "Bioelectrical Impedance Measurements as a Method of Screening for Peripheral Vascular Disease and Deep Venous Thrombosis" by Allan F. Pacela dated May 25, 1971, includes a comprehensive discussion of the background and utilization of bioelectrical impedance measurements. In addition the report discloses a number of instrumentation systems utilized in the prior art for bioelectrical impedance measuring.

One such instrumentation system is discussed in Section 5.5 of the Pacela report under the subheading of "Impedance Ratio Systems". FIG. 10 of the Pacela report and the above-identified section generally disclose an impedance ratio system wherein an excitation signal is coupled to the subject to be measured by excitation electrodes, and wherein a resulting subject output signal is sensed by receiver electrodes. The subject output signal is electronically subtracted from a reference level derived from the excitation source. In such a system, it is envisioned that the subject excitation signal be derived from a constant current source, and that the level of the constant current be adjusted so that the voltage across the sensing electrodes is always the same. This is accomplished by a balance control which is adjusted so that the d.c. level of the system output is at a known level, preferably a null condition. In that event the voltage drop across the receiver electrodes is at a known level and the system output represents a ratio of impedances ($\Delta Z_0/Z_0$) which is the desired function. In that event $Z_0$ is the steady "basal" value of impedance of the body segment, and $\Delta Z_0$ represents any variation in the basal value.

The impedance ratio system described hereinbefore has certain advantages in bioelectrical impedance measuring applications. However, a major disadvantage in the system is the difficulty of adjusting the excitation function to achieve a null condition throughout the normal range of subject impedance values. For example, the value of $Z_0$ can span a range of more than 10 to 1. Consequently, when maintaining currently accepted values of allowable subject excitation under present safety requirements, the excitation current in the impedance ratio system must be adjusted to a point where the excitation elements and controls of the system contribute appreciably to the noise level in the system. In addition, as is mentioned in the report, the system must be frequently rebalanced and thus is less useful in clinical applications. Finally, if a bilateral measurement is to be made, i.e. where two extremities of a subject are excited in series by the same excitation function, the electrode technique to achieve identical scale factors for each of the two receiver channels becomes hypercritical. Consequently the effective use of the system in such applications is nearly impossible.

SUMMARY OF THE INVENTION

Accordingly it is an object of the invention to provide a bioelectrical impedance measuring system that overcomes the disadvantages of the impedance ratio system described hereinbefore.

It is another object of the invention to provide such a bioelectrical impedance measuring system which includes means for achieving an automatic null condition in the system when in operation.

It is a further object of the invention to provide in a bioelectrical impedance measuring system of the impedance ratio type, a null detector associated with the instrument output and an automatic gain control unit, responsive to the null detector, connected in the subject output signal path for automatically maintaining the system in a null condition.

It is yet another object of the invention to provide, in such a bioelectrical impedance measuring system, a lock function generator in association with the automatic gain control unit to hold the variable gain of the system at an instantaneous null value for a desired measurement episode.

It is yet a further object of the invention to provide, in conjunction with the automatic nulling circuitry, a range indicating system which indicates to an operator that the basal impedance value of a given subject lies within the dynamic range of the instrument.

These and other objects of the invention are attained in a bioelectrical impedance measuring system wherein an excitation signal, derived from an electrical signal source, is coupled to the subject by excitation electrodes and a resulting subject output signal is sensed by receiver electrodes. The subject output signal is electronically subtracted from a reference signal, also derived from the signal source, and the resulting signal is used to drive a display unit. The system includes a null detector connected to the display unit input and an automatic gain control unit responsive to the null detector, connected in the subject output signal path to automatically maintain the system in a nulled condition. The automatic gain control unit includes a lock function generator to hold the variable gain of the system at instantaneous nulled values for one or more desired measurement episodes. Means can be provided, in conjunction with the automatic nulling circuitry, to indicate to an operator that the basal value of impedance of the given subject lies within the dynamic range of the instrument.

BRIEF DESCRIPTION OF THE DRAWINGS

The foregoing and other objects, features and advantages of the invention will become apparent hereinafter from the following detailed description of the invention taken in conjunction with the accompanying drawings wherein FIG. 1 comprises an electrical schematic diagram of one preferred embodiment of a bioelectrical impedance measurement system.

DETAILED DESCRIPTION OF THE INVENTION

Figure 1:
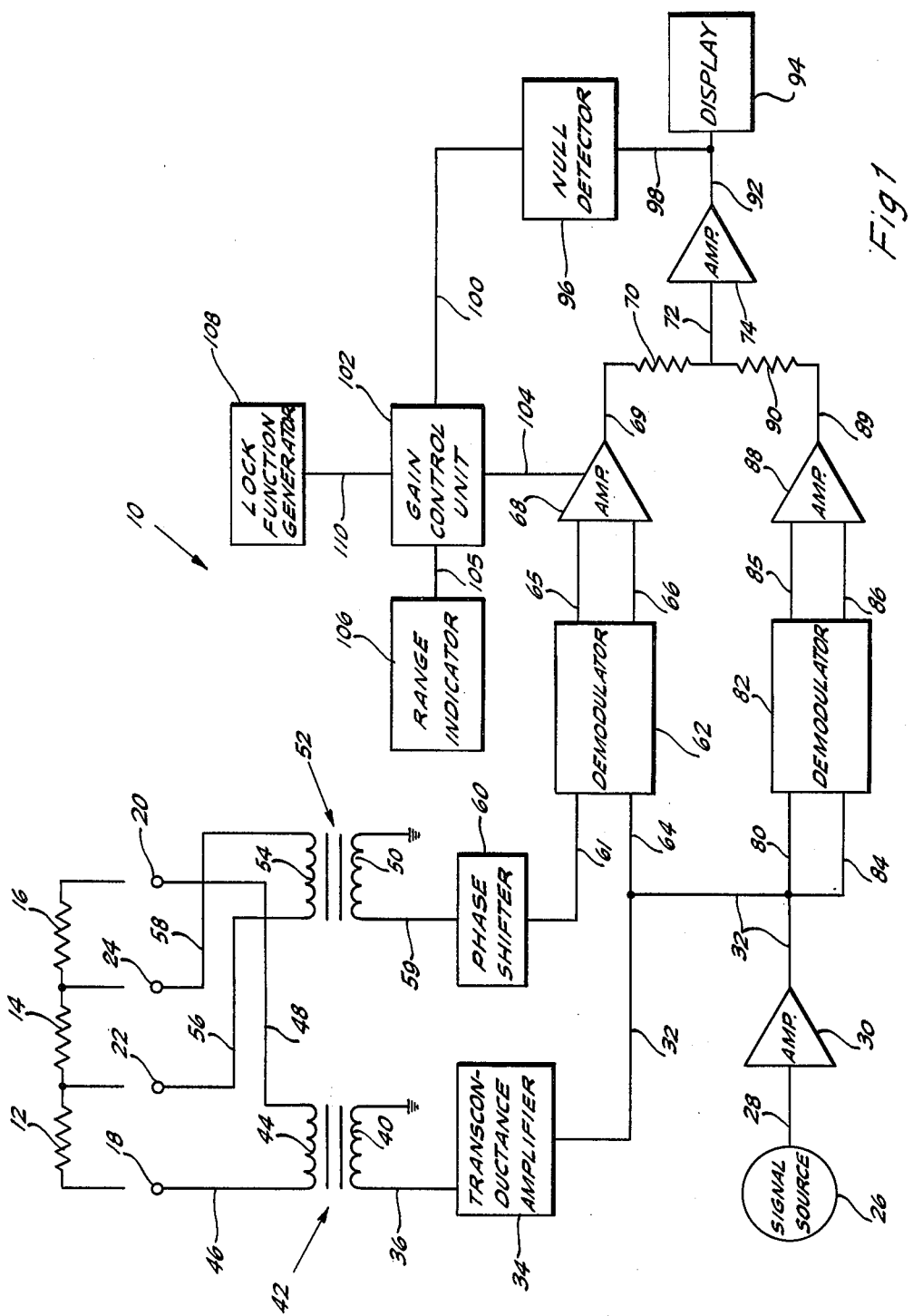

Referring now the the drawing, a preferred embodiment of the invention is described comprising a bioelectrical impedance measuring system 10 adapted for measuring the impedance of a subject, such as a section of human tissue or one or more human extremities, indicated by resistances 12, 14, 16 that generally extend between excitation electrodes 18, 20 and receiver electrodes 22, 24. Electrodes 18, 20, 22, 24 are schematically represented in coupled relationship to the subject represented by the above-identified resistances. It is envisioned that the coupling be made by conventional electrodes, such as metallic band surface electrodes. However other types of coupling can be utilized, if desired, for particular purposes.

The system also includes a signal source 26 comprising a high frequency signal source. The signal source is of conventional design and is used to provide power for subject excitation and for reference signal derivation. Signal source 26 is connected via a conductor 28 to the input of a voltage amplifier 30 which provides a low impedance driving source. The output of amplifier 30 is connected via conductor 32 to the input of a transconductance amplifier 34. Amplifier 34 is of conventional design and provides a given output current in response to a given input voltage. The output signal of amplifier 34 is supplied via conductor 36 to one terminal of a primary winding 40 of a transformer 42. The other terminal of winding 40 is connected to ground. Transformer 42 isolates the subject to be measured from common mode, low frequency and D.C. differential signals, and also provides impedance matching in the signal path. One terminal of secondary winding 44 of the transformer is connected via conductor 46 to excitation electrode 18 and the other terminal of winding 44 is connected via a conductor 48 to excitation electrode 20. The characteristics of amplifier 34 and transformer 42 combine to produce an effective source impedance which is very high compared to the impedance of the subject, thereby producing a substantially constant current source system.

A transformer 52 is also provided having a primary winding 54 that has one terminal connected via conductor 56 to receiver electrode 22 and another terminal connected via conductor 58 to receiver electrode 24. A secondary winding 50 of transformer 52 has one terminal connected to ground and the other terminal connected via a conductor 59 to a phase shift circuit 60 and then via conductor 61 to one input terminal of a demodulator 62. Phase shift circuit 60 compensates for parasitic phase shifts occurring in the measuring apparatus. Demodulator 62 has a second input terminal which is connected via conductors 32, 64 to the output of amplifier 30. Demodulator 62 is a conventional synchronous demodulator that produces a d.c. output signal having a level proportional to the RMS value of an alternating input voltage. The use of a synchronous demodulator makes it insensitive to phase shift in the signal caused by subject reactance. Consequently the output of the demodulator represents only the resistance component of the subject impedance. It should be apparent that other means of deriving a d.c. signal could be used, if the demodulator output is to represent total impedance of the subject. The output of demodulator 62 is provided via conductors 65, 66 to the inputs of an amplifier 68. Amplifier 68 is a conventional d.c. amplifier utilized to condition the output of demodulator 62. The output of amplifier 68 is provided via a conductor 69, a resistor 70 and a conductor 72 to the input terminal of an amplifier 74.

Another synchronous demodulator 82 is provided receiving an input signal via conductors 32, 80 from amplifier 30 and another input signal via conductors 32, 84 from amplifier 30. Demodulator 82 is a conventional unit, similar to demodulator 62, that provides a d.c. level output proportional to the RMS value of the alternating output of amplifier 30. The output of demodulator 82 is provided via conductors 85, 86 to the input terminal of an amplifier 88. Amplifier 88 is a conventional d.c. amplifier having an output signal that is provided via conductor 89, resistor 90 and conductor 72 as the second input signal to amplifier 74. The output of amplifier 88 is of opposite polarity to the output of amplifier 68. Accordingly amplifier 74, which is a conventional d.c. summing amplifier, serves to electronically combine the output signals of amplifiers 68, 88 respectively. Amplifier 74 produces an output signal which is connected via a conductor 92 to an input terminal of a display unit 94. Display unit 94 can comprise any suitable type of display adapted to indicate the measured value of $(\Delta Z_0/Z_0)$ or $(\Delta R_0/R_0)$ as measured by the system.

The bioelectrical impedance measuring system described herein further includes a null detector 96 having an input terminal electrically connected via conductors 92, 98 to the output of amplifier 74. Null detector 96 is a conventional unit adapted to produce an output signal that reflects the absence of a null condition. The output of null detector 96 further indicates whether the output of amplifier 74 is of positive or negative polarity, i.e. whether the subject signal is greater or less than the reference signal. The output of detector 96 is connected via a conductor 100 to an input terminal of a gain control unit 102. Gain control unit 102 provides an output signal which is connected via a conductor 104 to amplifier 68 to controllably vary the gain thereof. Accordingly null detector 96 and gain control unit 102 function as a feedback type system to automatically achieve null balance in the system by varying the gain of amplifier 68. A lock function generator 108 is provided having an output that is connected via a conductor 110 to gain control unit 102. Lock function generator 108 selectively provides a lock function signal to gain control unit 102 that is effective to hold the variable gain of the system at a given null value for a predetermined period which comprises a measurement episode. The lock function generator can be operator actuated, or means can be provided to actuate the generator at predetermined measurement intervals. The output of gain control unit 102 is also connected via conductor 105 to a range indicator unit 106. The range indicator provides a signal which indicates that the range of effective gain control has not been exceeded. This verifies that the subject impedance lies within the lower dynamic range of the instrument.

In the operation of the system described herein the subject is excited by a signal from source 26 delivered via amplifier 30, transconductance amplifier 34 and transformer 42 via excitation electrodes 18, 20. The signal utilized is a high frequency signal magnitude which is well within accepted risk standards for electrically susceptible human subjects. A subject output signal is derived from receiver electrodes 22, 24 and coupled via isolation transformer 52 to the phase shift circuit 60, the input of demodulator 62, and amplifier 68 to produce a d.c. output which has an amplitude proportional to the RMS value of the alternating subject output signal. This output is compared in summing amplifier 74 with a reference signal which is derived from source 26, synchronously demodulated by demodulator 82 and amplifier 88, and supplied to amplifier 74 with an opposite polarity to the signal from amplifier 68. Accordingly when a null signal is achieved at the output of amplifier 74 it represents the value ($\Delta Z_0/Z_0$) or ($\Delta R_0/R_0$) or the ratio of variations in the basal value of impedance to the basal value itself.

The output signal from amplifier 74 is utilized to drive the display unit whereby the value can be determined by an operator. The null detecting circuit 96 senses any deviation from a null condition and produces a feedback signal which is supplied to gain control unit 102 and ultimately results in variation of the gain of amplifier 68 to maintain the null condition, automatically. The lock function generator can be utilized by the operator to freeze the gain of the subject output signal path for a predetermined time establishing a basal value for an ensuing measurement episode.

The range indicator allows the operator to verify whether the value $Z_0$ of a given subject lies within the dynamic range of the instrument. This enables the adjustment of gain, automatically, in the subject output signal path over a 10 to 1 range of variation without risk or receiving unreliable signals.

Figure 2:
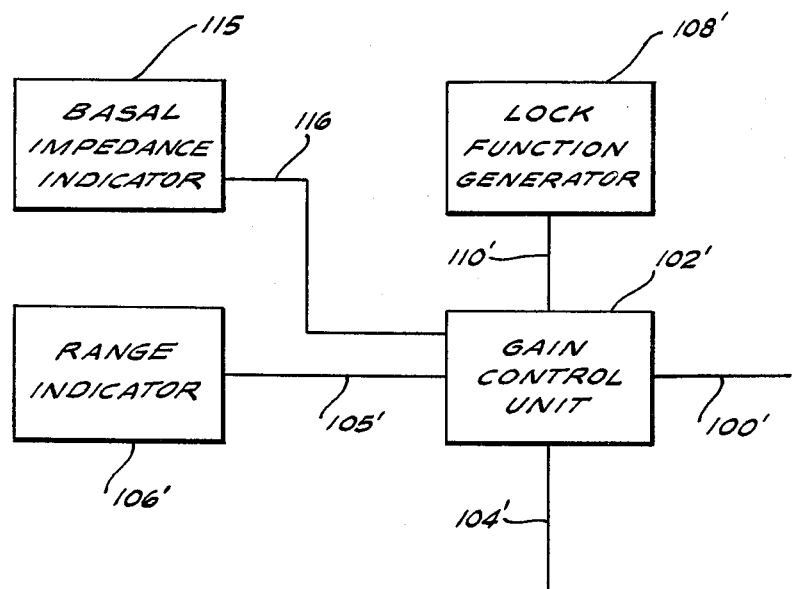
FIG. 2 comprises a partial schematic diagram illustrating an alternative preferred embodiment.

In an alternative form of the invention a second display can be included such as that illustrated in FIG. 2 wherein like elements of FIG. 1 are indicated by like primed numerals. In FIG. 2 a basal value indicator 115 is connected to gain control unit 102'. Indicator 115 is responsive to signals from the gain control unit and displays the basal impedance or resistance of the subject. Indicator 115 can comprise a digital or an analog display. The indicator can be utilized in a tracking mode in which a continuous display of values is provided, or it can be set to a measurement episode mode wherein it is actuated by a lock function generator 108' to provide a display of the basal impedance value that exists during a given measurement episode.

Figure 3:
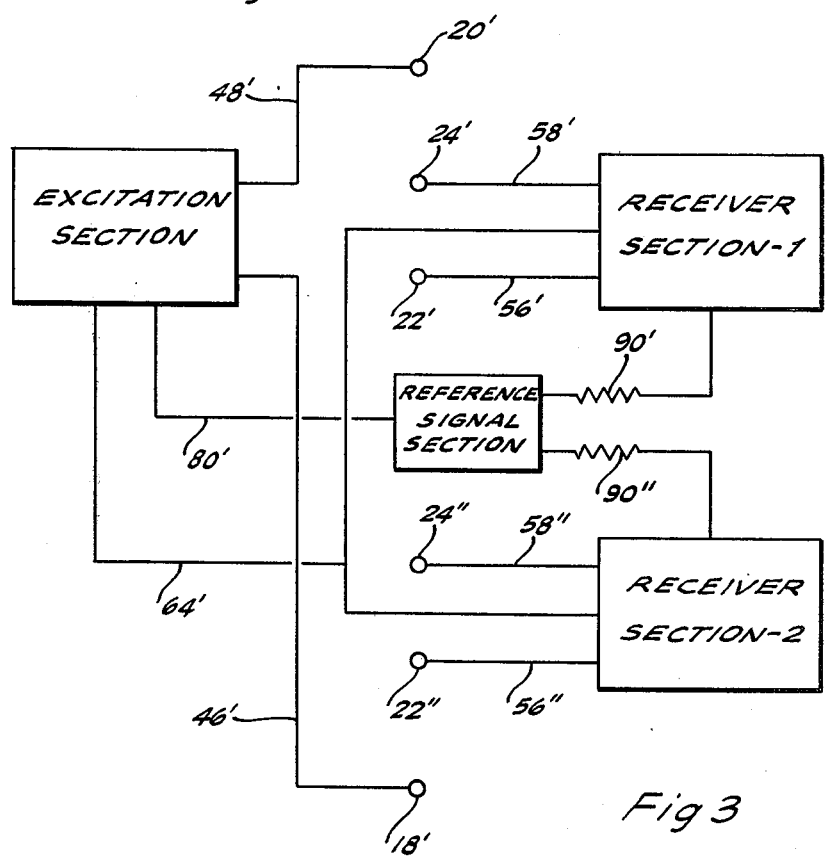
FIG. 3 comprises a block diagram illustrating a modification of the FIG. 1 embodiment.

Referring particularly to FIG. 3, another alternative form of the invention is illustrated wherein like numerals of FIG. 1 are illustrated by like double primed characters. In FIG. 3 a single excitation section of the instrument is adapted for use with two or more sensing sections of the instrument, as illustrated. As shown, excitation electrodes 18', 20' are positioned as in the embodiment of FIG. 1, and each receiver section includes a pair of receiver electrodes 22', 24' and 22'', 24'' respectively. The respective receiver sections are each adapted to receive a reference signal from the excitation section via resistors 90', 90'', respectively. In addition the receiver sections share line 64' which interconnects the excitation signal line 32 with the appropriate demodulator of the respective receiver sections.

The embodiment illustrated permits the use of the instrument to excite multilateral systems since the receivers can be independently nulled providing identical output scale factors while using the common excitation source. This enables multilateral measurements to be taken, such as simultaneous measurements of the impedance of each leg of a subject, for example.

The present system has several advantages over prior art bioelectrical impedance measuring systems. In particular this system utilizes a fixed excitation current from oscillator 26. However, the system includes an automatic null function which is achieved by controlling the gain in one signal path of the instrument. The automatic null adjustment removes operator skill in adjusting controls, and the lock function enables accurate measurements to be taken during desired measurement episodes in which the variable gain is held at the null value.

As a result of these features, a fixed predetermined excitation current can be established at a large, but safe level regardless of basal impedance of the subject. The automatic null function is accomplished in a large signal environment, i.e. the amplifier near the output stage in the instrument, thereby providing a signal-to-noise ratio which is improved by a factor equal to the gain of the amplification in front of it. The excitation source in the system can be used to excite multilateral systems, as well, since the receivers can be independently nulled. The range indicator ensures that the operator can verify that the basal impedance of the subject is within the dynamic range of the instrument.

I claim:

1. A bioelectrical impedance measuring system comprising
  excitation electrode means adapted to be associated with a subject exhibiting impedance to be measured, for coupling a high frequency excitation signal to the subject;
  receiver electrode means adapted to be associated with the subject for receiving a subject output signal developed in response to the excitation signal;
  subject signal amplifier means connected to said receiver electrode means for developing a d.c. output signal proportional to the subject output signal;
  reference amplifier means adapted to be connected to the source of the high frequency excitation signal for developing a d.c. reference signal from the excitation signal;
  differencing means connected to said subject signal amplifier means and to said reference amplifier means for deriving a difference signal proportional to the amplitude difference between said d.c. subject signal and said d.c. reference signal;
  detecting means connected to said differencing means for detecting a nulled condition of said difference signal;
  gain control means for adjusting and stabilizing the gain of said subject signal amplifier means with said difference signal in a nulled condition; and display means connected to said differencing means responsive to said difference signal.

2. The bioelectrical impedance measuring system of claim 1 wherein said gain control means includes circuit means responsive to said detecting means for automatically adjusting the gain of said subject signal amplifier means to achieve a nulled condition of said difference signal; and
lock function generator means connected to said circuit means for maintaining the gain of said subject signal amplifier at said adjusted value for a predetermined measurement episode.

3. The impedance measuring system of claim 2 further including
indicator means associated with said gain control means for indicating whether the value of said difference signal is within a predetermined range.

4. The impedance measuring system of claim 3 further including
a basal value indicator means for displaying a value derived from said gain control means that is proportional to the basal impedance of the subject.

5. In a bioelectrical impedance measuring system for measuring and indicating the basal impedance value of a subject and short variations in the basal value, wherein a high frequency excitation signal is applied to the subject from a suitable signal source and the resultant subject signal developed in response thereto is received, amplified in a subject signal amplifier and compared in a comparator with a reference signal developed from the signal source to obtain a difference signal, the improvement comprising:
means for amplifying the difference signal from the comparator,
means for detecting a nulled condition of said amplified difference signal;
gain control means for adjusting the gain of said subject signal amplifier to establish said amplified difference signal at the nulled condition; and
lock function generator means for maintaining the gain of said subject signal amplifier at the adjusted value for a predetermined measurement episode.

6. The bioelectrical impedance measuring system of claim 5 further including
display means connected to said amplifying means responsive to said difference signal.

7. A bioelectrical impedance measuring system for measuring and indicating a basal impedance value of a measured subject as well as short variations in the basal value, comprising
at least one set of excitation electrodes adapted to be electrically coupled between a source and said subject for transmitting a high frequency excitation signal to the subject;
at least one set of receiver electrodes adapted to be electrically associated with said subject for receiving a subject signal developed in response to the excitation signal;
synchronous demodulator means connected to said receiver electrodes for providing a d.c. output signal proportional to said subject output signal;
subject output signal amplifier means connected to said synchronous demodulator means for amplifying said d.c. output signal;
second synchronous demodulator means adapted to be connected to said source for developing a d.c. reference signal proportional to said excitation signal;
reference signal amplifier means connected to said second synchronous demodulator means for amplifying said d.c. reference signal;
summing amplifier means connected to each of said signal amplifier means for deriving an amplified signal proportional to the amplitude difference between said d.c. output signal and said d.c. reference signal;
null detecting means connected to said summing amplifier means for detecting a nulled condition of said amplified signal;
gain control means connected between said null detecting means and said subject output signal amplifier means for adjusting the gain of said subject output signal amplifier means to establish said amplified difference signal at a nulled condition;
lock function generator means connected to said gain control means for maintaining the gain of said subject output signal amplifier means at said adjusted value for a predetermined measurement episode; and
display means connected to said summing amplifier for displaying said amplified signal.

8. A method of measuring the impedance of a bioelectrical subject comprising the steps of
applying a high frequency excitation signal to the subject;
receiving a subject excitation signal therefrom developed in response to said excitation signal;
amplifying the subject output signal in an amplifier;
comparing in a comparator the amplified subject output signal and a reference signal derived from said excitation signal;
adjusting the gain of the amplifier to establish the output signal of the comparator at a level approximating a nulled condition; and
maintaining the adjusted gain of the amplifier for a predetermined measurement episode to permit measurement of variations in the subject output signal.

* * * * *